(12) United States Patent
Heimberg et al.

(10) Patent No.: US 7,201,880 B1
(45) Date of Patent: Apr. 10, 2007

(54) SAMPLE DISPENSER

(75) Inventors: Wolfgang Heimberg, Ebersberg (DE); Christina Schmidt, Ebersberg (DE)

(73) Assignee: F. Hoffman-LaRoche AG, Basel (CH)

( * ) Notice: Subject to any disclaimer, the term of this patent is extended or adjusted under 35 U.S.C. 154(b) by 0 days.

(21) Appl. No.: 10/048,132

(22) PCT Filed: Mar. 17, 2000

(86) PCT No.: PCT/EP00/02412

§ 371 (c)(1),
(2), (4) Date: Jun. 12, 2002

(87) PCT Pub. No.: WO01/12328

PCT Pub. Date: Feb. 22, 2001

(30) Foreign Application Priority Data

Aug. 17, 1999 (DE) .......................... 299 14 360 U (51) Int. Cl.
*B01L 3/02* (2006.01)
(52) U.S. Cl. .................. 422/100; 422/99; 422/101; 222/583; 101/494; 436/180; 73/864.02
(58) Field of Classification Search .......... 422/99–101; 436/180; 222/583; 73/864.02; 101/494
See application file for complete search history.

(56) References Cited

U.S. PATENT DOCUMENTS

| 4,076,503 A | 2/1978 | Atwood et al. |
| 4,162,896 A | 7/1979 | Hosli |
| 5,756,050 A | 5/1998 | Ershow et al. |

(Continued)

FOREIGN PATENT DOCUMENTS

DE     3016682     11/1980

(Continued)

OTHER PUBLICATIONS

German Patent Office Search Report for Application No. 29914360.0, four pages, dated Dec. 28, 1999.

(Continued)

*Primary Examiner*—Jill Warden
*Assistant Examiner*—Jyoti Nagpaul
(74) *Attorney, Agent, or Firm*—Rankin, Hill, Porter & Clark LLP (57) ABSTRACT

The invention relates to a sample dispenser, for the application of liquid samples on to a sample absorbing area, with a sample dispenser body (1) having at its end a sample pick-up surface (5) bounded by a continuous edge (6), wherein the sample pick-up surface (5) is provided with a recess (7) such that, when the sample pick-up surface (5) is dipped into a sample reservoir, a droplet of liquid sample of predetermined size adheres to the sample pick-up surface (5) and by placing of the sample pick-up surface (5) on the sample absorbing area is completely dispensed, and wherein the recess (7) is in the form of a flat recess (7), that is to say, it has a depth which is less than its width.

The sample dispenser according to the invention is of very simple design. In using it, the desired sample amount to be transferred is determined by the flat recess of the sample pick-up surface and can be reproduced very precisely.

14 Claims, 7 Drawing Sheets

U.S. PATENT DOCUMENTS

| | | | |
|---|---|---|---|
| 5,882,930 A | 3/1999 | Baier | |
| 6,101,946 A * | 8/2000 | Martinsky | 101/494 |
| 6,116,297 A * | 9/2000 | Feygin | 141/31 |
| 6,555,386 B1 * | 4/2003 | Rees | 436/180 |

FOREIGN PATENT DOCUMENTS

| | | | |
|---|---|---|---|
| DE | 4136217 A1 | 5/1993 | |
| DE | 19700626 A1 | 7/1999 | |
| EP | 0635710 | * | 7/1994 |
| EP | 0635710 A2 | 1/1995 | |
| WO | WO 93/09872 | 5/1993 | |
| WO | WO 98/55852 | 5/1993 | |
| WO | WO 98/57747 | 12/1998 | |
| WO | WO 00/25923 | 5/2000 | |

OTHER PUBLICATIONS

International Search Report for PCT/EP00/02412. dated Jul. 19, 2002, four pages.

* cited by examiner

SAMPLE DISPENSER

The invention relates to a sample dispenser for the application of liquid samples to a sample absorbing area.

Sample dispensers for the transfer of very small amounts of sample are known, in which a capillary may be used to draw in a liquid sample and deliver it to a sample area. For this purpose the sample area must have an absorbent material which sucks the sample liquid from the capillary. The capillary of this sample dispenser is inserted into a thin spring leaf, as in a fountain pen. With a sample dispenser of this kind, very small quantities can be absorbed very precisely, since the amount is defined exactly by the capillary. However, it has been found that delivery of the sample amount held in the capillary involves considerable problems, since the absorbent material forming the sample absorbing area requires a very strong suction effect, otherwise residues of the sample liquid remain in the capillary. These sample dispensers with capillary are therefore usable only for special sample absorbing areas and it is also difficult to use such sample dispensers in an automated process which does not always involve a check as to whether or not the sample liquid held in the capillary is being completely transferred to the sample absorbing area.

Known from DE 197 00 626 A1 is a membrane comb made from a porous material such as e.g. a nylon membrane coated with hydroxyl groups. A sample amount of around 0.2 to 0.3 microliters should be applied to each individual tooth of this membrane comb. The sample material is e.g. DNA in formamide. In transferring the sample material to the teeth of this membrane comb, it was not possible to obtain a satisfactory result in transferring the sample liquid to the individual teeth of the membrane combs.

Also known are sample dispensers in the form of tips, with which it should be possible to transfer metered amounts of viscous media. These sample dispensers have, however, proved unsuccessful for the application described above involving the metered transfer of formamide, since no drops or else only drops containing widely varying amounts adhere to it.

WO 93/09872 describes a plate with reaction vessels (e.g. FIG. 5), similar in form to a micro-titration plate. A metering device is provided to supply chemicals. This metering device has projections to which drops of chemicals can adhere. These projections are in part in the form of hollow-cylindrical bodies.

WO 98/57747 discloses a further sample dispenser which is in the form of a rod with a wettable tip and non-wettable sides. In this patent application it is specified that the rod may in principle have any desired cross-section (oval, polygonal, etc.), and that it may be made of glass or any other material.

DE 30 16 682 A1 relates to a blood serum applicator. The applicator described therein has a porous section by which the blood serum is transferred. Prior art is described in this patent application, and illustrated in FIGS. 1A to 2B which show a sample dispenser with recesses in which the sample is held by capillary forces.

Described in U.S. Pat. No. 5,882,930 is a sample dispenser formed of a transfer element on which pins are arranged in a regular grid pattern. Sample droplets are able to adhere to the free tips of the pins. The pins have preferably a diameter of 30 µm to 100 µm and are cylindrical.

WO 98/5852 describes a sample applicator with pins fastened to a holding structure. The pins are so thin that their tips become surrounded by drops.

Described in U.S. Pat. No. 5,756,050 is a further sample dispenser which has a bar with a conical tapered tip. The end of the tip is provided with a hydrophilic coating. A hydrophobic coating is applied to the adjacent surfaces.

The invention is based on the problem of creating a sample dispenser for the application of liquid samples to a sample absorbing area, which is of simple design, can reliably take up and reliably transfer to a sample absorbing area small sample volumes (<1 microliter), and is suitable for automatic operation in which not every sample take-up and every sample delivery can be checked individually.

The problem is solved by a sample dispenser with the characteristics of claim 1. Advantageous developments of the invention are specified in the subsidiary claims.

The sample dispenser according to the invention for the application of liquid samples to a sample absorbing area is formed by a sample dispenser body with a sample pick-up surface. The sample pick-up surface is bounded by a continuous edge and is provided with a flat recess such that, when the sample pick-up surface is dipped, a droplet of liquid sample of predetermined size adheres to the sample pick-up surface and is dispensed by placing of the sample pick-up surface on the sample absorbing area.

Tests have shown that, with the sample dispenser according to the invention, the desired amounts of liquid samples are reliably taken up solely by dipping the sample pick-up surface into the liquid sample, and reliably dispensed solely by placing on the sample absorbing area. The sample absorbing area has preferably a certain absorbency which, however, may be significantly less than that required in the use of the sample dispensers with capillaries described above.

The sample dispenser according to the invention is very simple in design; the sample quantity which it is desired to transfer is set by the recess of the sample pick-up surface and is reproducible with surprising exactness. The sample quantity is influenced by the physical properties, in particular the surface tension, of the sample liquid. The greater the surface tension of the sample liquid, the larger are the liquid droplets transferred by the sample dispenser according to the invention. The nature of the sample liquid is therefore to be taken into account in dimensioning the recess of the sample pick-up surface.

In the course of developing the present invention, various types of sample dispenser have been tested, e.g. pipette tips, steel capillaries, glass capillaries and various sample dispensers with long grooves or notches. With all these sample dispensers, the problems described above regarding transfer of the sample liquid to the sample absorbing area occurred.

Also tested was a sample dispenser with a flat sample pick-up surface of predetermined size, in which the surface had been roughened. While this embodiment certainly allowed for reliable transfer of the sample liquid to the sample absorbing area, sample droplets of widely varying size were taken up on dipping into the sample liquid, so that with this sample dispenser too it is not possible to transfer a reproducible sample quantity.

Only the sample dispenser according to the invention has met the requirements satisfactorily, so that it may also be used in an automatic process.

The invention is described in detail below with the aid of the embodiments depicted in the drawings, which show.

FIGS. 1 to 5 show a first embodiment of the sample dispenser according to the invention. The sample dispenser according to the invention has a sample dispenser body 1 made of an aluminium alloy, comprising a rod-shaped shank section 2, a conical tapering transition section 3, and a tip 4 connected to the conical tapering transition section 3. The tip 4 is cylindrical in shape. The length of the shank section 2 is roughly 20 mm, that of the transition section 3 roughly 19 mm, and the length of the tip 4 is approx. 2 mm. The diameter of the tip is approx. 1 mm.

The free end of the tip 4 forms a sample pick-up surface 5. In the present embodiment the sample pick-up surface 5 is circular (FIG. 3, FIG. 5), so that it is bounded by a circular edge 6. The sample pick-up surface 5 is provided with a conical recess 7, arranged concentrically to the longitudinal axis 8 of the sample dispensers, while the conical surfaces formed by the conical recess end at the edge 6 which bounds the sample pick-up surface 5. The angle α which encloses the conical recess lies in the range 90° to 150°, and in the depicted embodiment is 120°. A recess of this kind is easily made with a drilling tool. The recess 7 made with a drilling tool has smooth inner surfaces which require no finishing apart from deflashing of the edges. It has been shown that a smooth sample pick-up surface 5 is advantageous since it allows better transfer of the sample liquid from the sample dispenser to a sample absorbing area. If the recess 7 is made by a method other than drilling, in which the surface is roughened, it is expedient for the surface to be smoothed by polishing.

Introduced from the upper end of the shank section 2, concentric to the longitudinal axis 8, is a hole 9 extending as far as the transition section 3. Introduced in the area of the upper end of the sample dispenser body 1, at right-angles to the hole 9, is a tapped hole 10. A locating bar of an operating device, e.g. of a robot for amplifying or sequencing DNAs, may be inserted in the hole 9 and fixed by means of a screw screwed into the tapped hole 10. The sample dispenser according to the invention is fastened to the operating device with the sample pick-up surface 5 facing downwards.

In operation the sample dispenser with its sample pick-up surface 5 is dipped into a sample reservoir, causing a sample droplet to be taken up by the sample pick-up surface 5. The size of the droplet is determined by the sample pick-up surface 5 and the recess 7. The sample droplet adheres to the sample pick-up surface 5 due to wetting forces, which are generally van-der-Waals forces. The sample dispenser is then placed on the sample absorbing area by its sample pick-up surface 5, with the sample pick-up surface 5 being pressed on to the sample absorbing area. By this means, the sample droplet adhering to the sample pick-up surface 5 is completely transferred to the sample absorbing area. If the recesses 7 are deeper it may be expedient to make the sample absorbing area flexible, for example by providing a suitable backing, so that the sample absorbing area is pressed into the recess 7 when the sample dispenser is pressed on to it, and completely absorbs the sample liquid contained therein.

It has been found expedient for the depth of the trough-shaped recess 7 to be no greater than 50% of the diameter of the sample pick-up surface 5.

Cleaning of the sample dispenser according to the invention is effected by pressing into a wetted foam material, by which means the recess 7 and the adjacent surface of the sample dispenser are cleaned. The foam material is open-celled and is wetted with water. However it is also possible to add a cleansing agent to the water.

Figure 1:
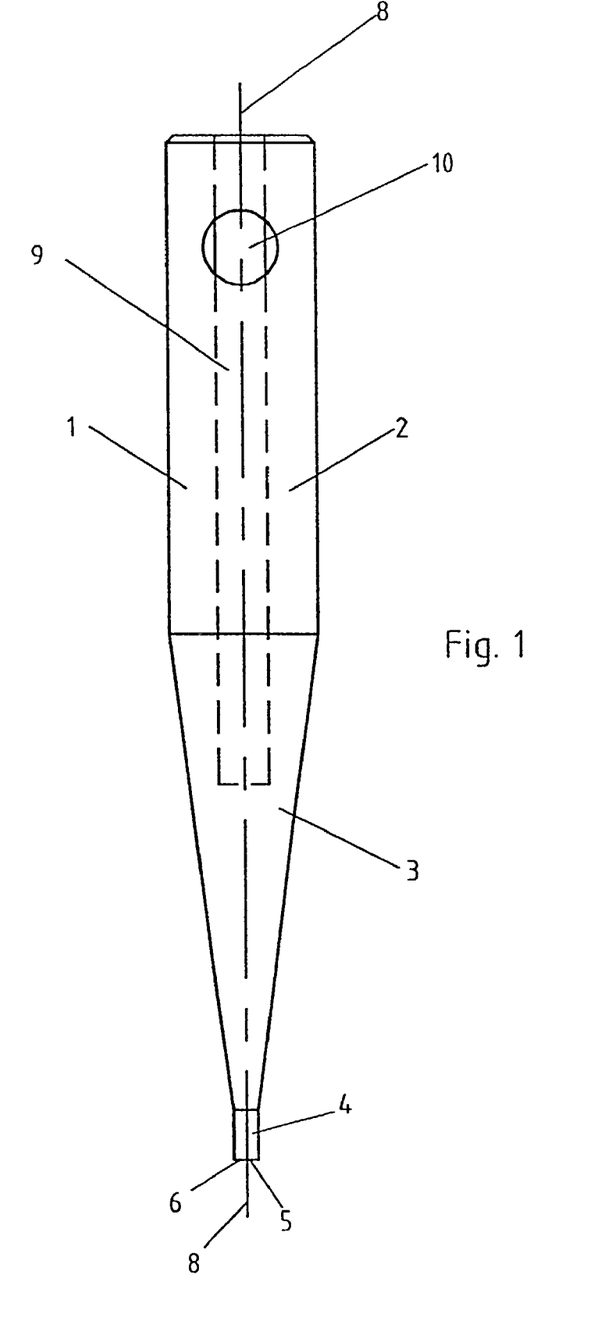
FIG. 1 a side view of a first embodiment of a sample dispenser according to the invention FIG. 2 the sample dispenser according to FIG. 1 in longitudinal section FIG. 3 a perspective view of the sample dispenser according to FIG. 1 viewed diagonally from above FIG. 4 an enlarged section of the tip of the sample dispenser according to FIG. 1
Figure 2:
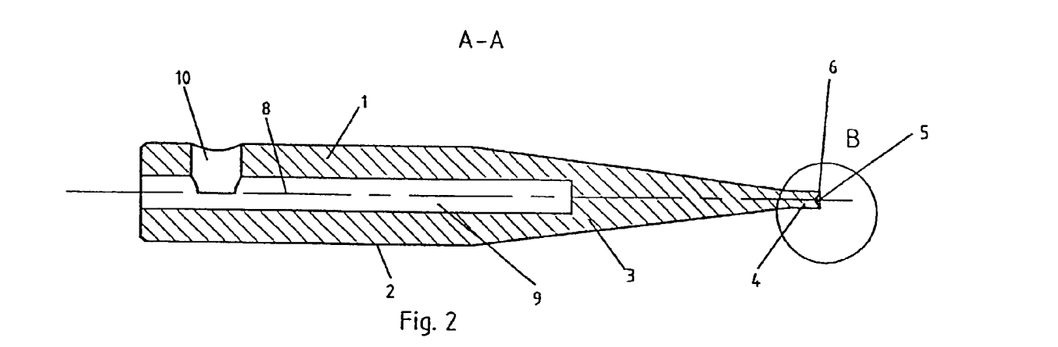
Figure 3:
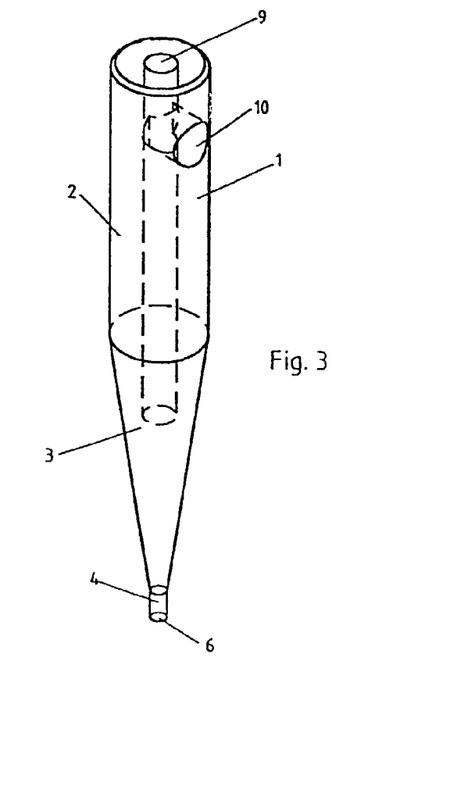
Figure 4:
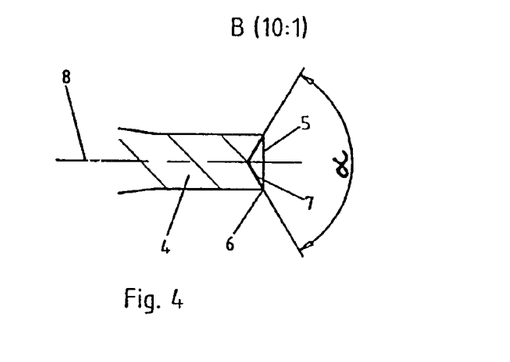
Figure 5:
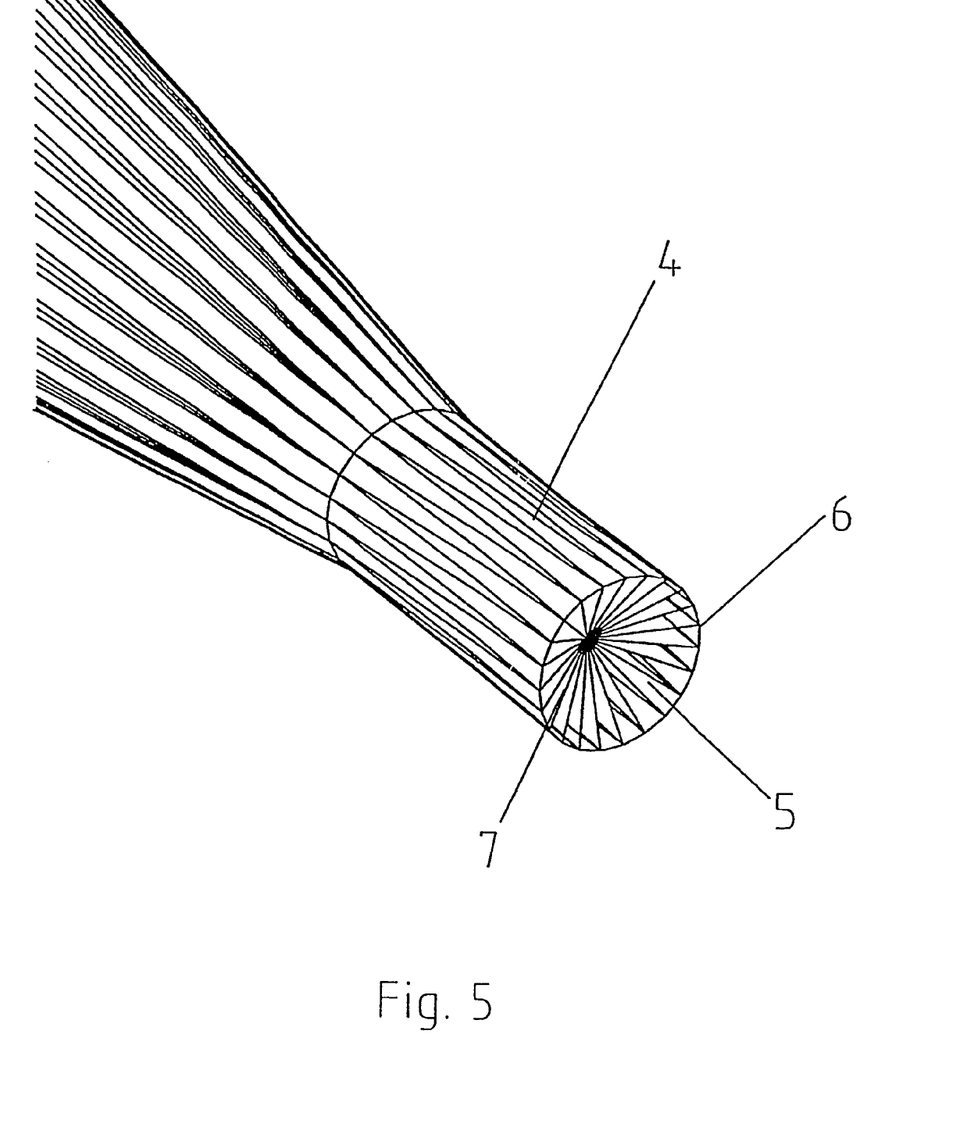
FIG. 5 a perspective view of the tip of the sample dispenser according to FIG. 1 viewed diagonally from below FIG. 6 a side view of a second embodiment of a sample dispenser according to the invention FIG. 7 the sample dispenser according to FIG. 6 in longitudinal section FIG. 8 a perspective view of the sample dispenser according to FIG. 6 viewed diagonally from above FIG. 9 an enlarged section of the tip of the sample dispenser according to FIG. 6
Figure 6:
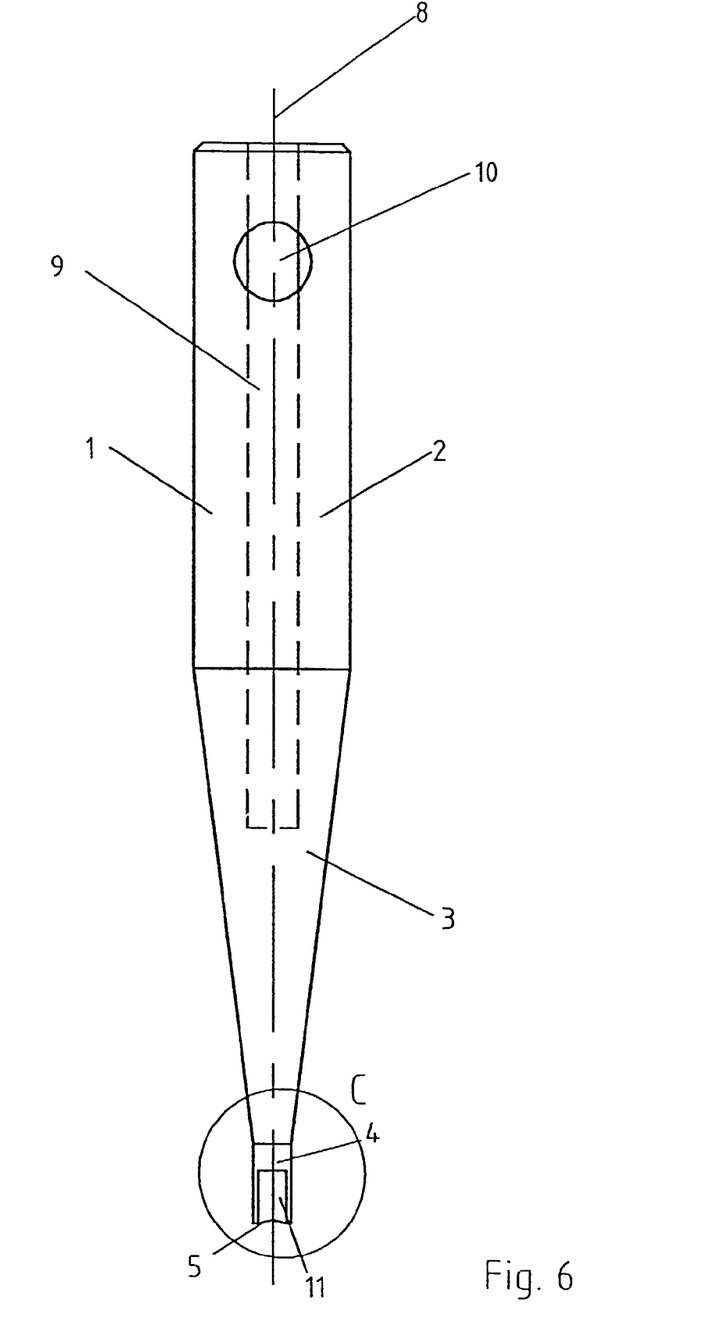
Figure 7:
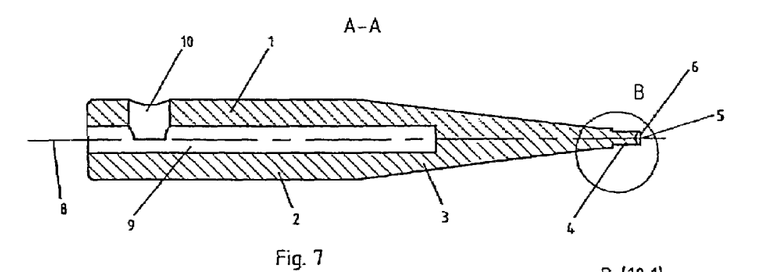
Figure 8:
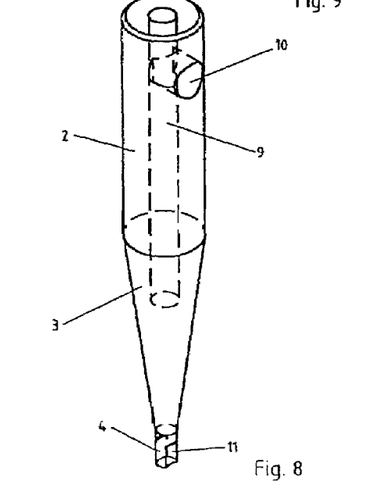
Figure 9:
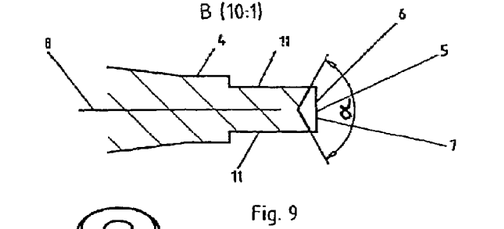
Figure 10:
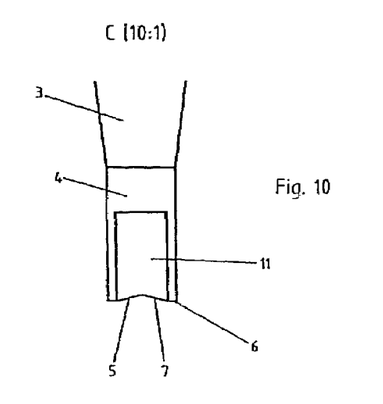
FIG. 10 an enlarged view of the tip of FIG. 6 seen from the side
Figure 11:
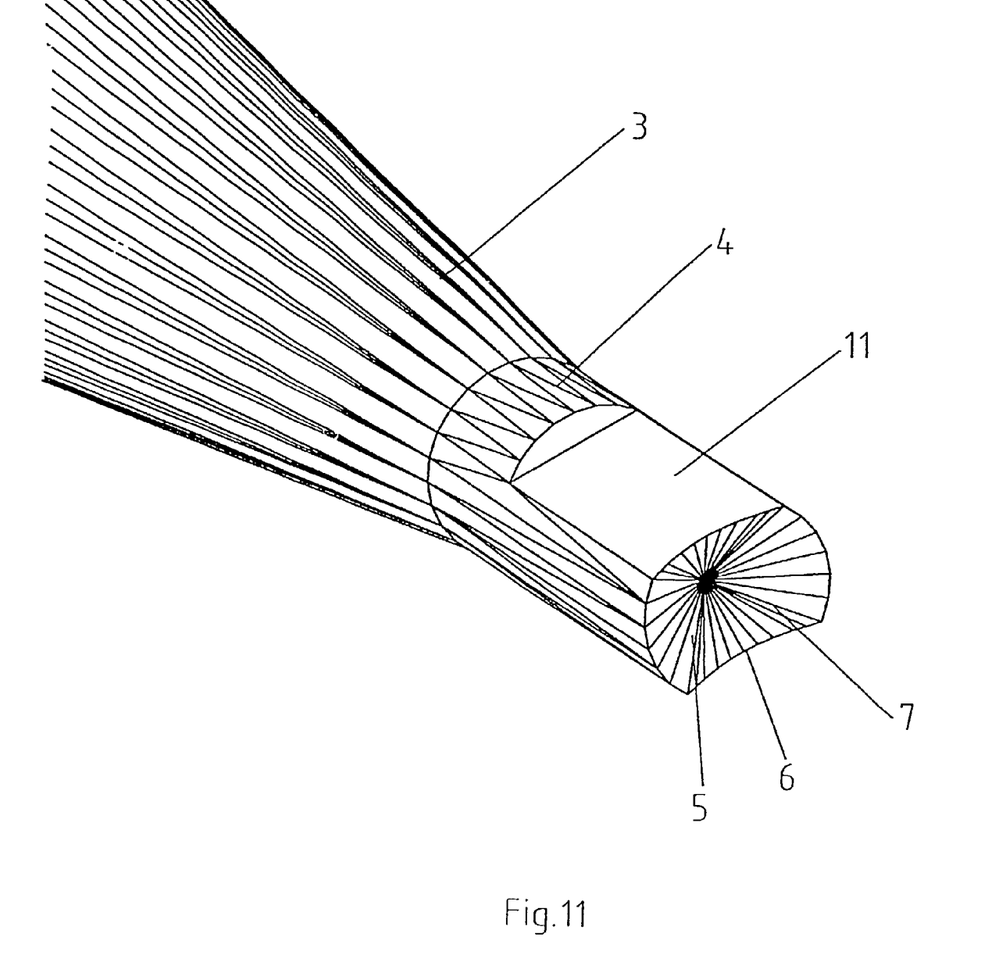
FIG. 11 a perspective view of the tip of the sample dispenser according to FIG. 6 viewed diagonally from below.
Figure 12:
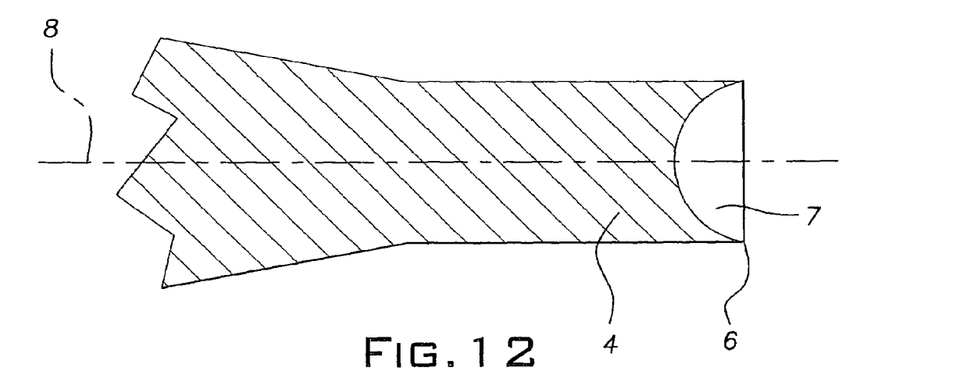
FIG. 12 an enlarged section of the tip of the sample dispenser having a recess in the shape of a segmented hollow sphere.
Figure 13:
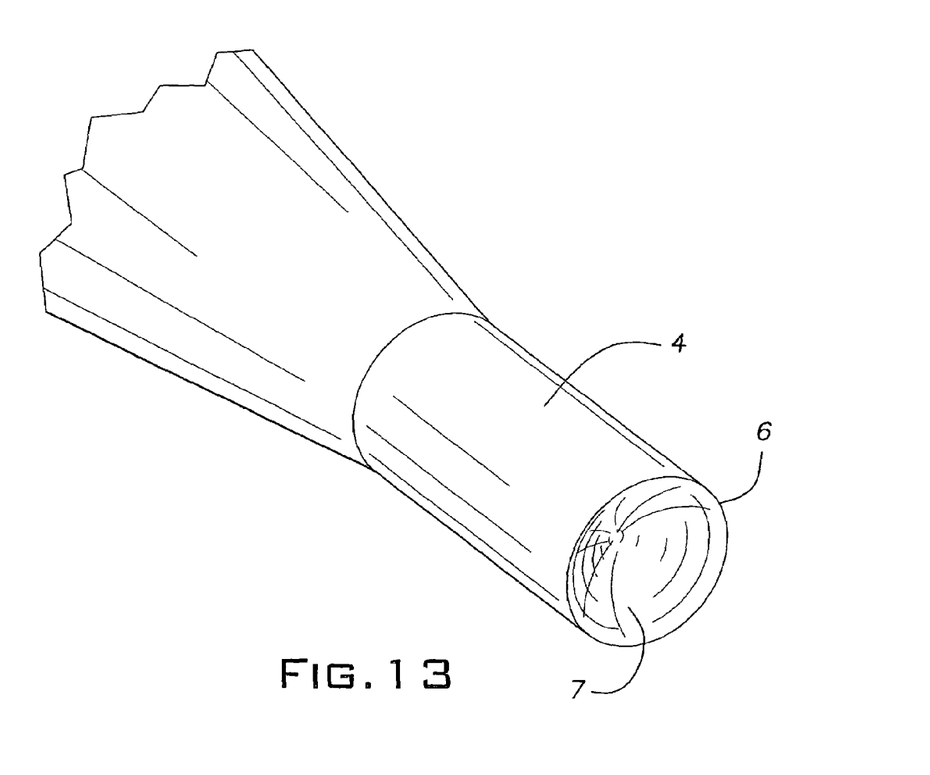
FIG. 13 a perspective view of the tip of the sample dispenser according to FIG. 12 viewed diagonally from below.

FIGS. 6 to 11 show a second embodiment of the sample dispenser according to the invention, substantially similar to the first embodiment, for which reasons identical parts are denoted by the same reference number. The only difference from the first embodiment lies in the fact that the cylinder of tip 4 has a greater diameter, namely 1.5 mm, and that tip 4 is flattened into two parallel surfaces 11 in the area of the circumferential surface of the cylinder bordering the sample pick-up surface 5 (FIGS. 9 to 11). The two flattened surfaces 11 are arranged at a distance d of approx. 1 mm from one another. Viewed from below (FIG. 11) this gives a roughly rectangular sample pick-up surface 5 with short side edges bent outwards.

As compared with the first embodiment, the second embodiment has a greater sample pick-up surface 5, so that it may also be used to take up larger sample droplets. However, the distance between the parallel surfaces 11 is no greater than the diameter of the sample pick-up surface 5 of the first embodiment, so that the sample dispenser according to the second embodiment may also be fitted against sample absorbing areas with limited space, e.g. the teeth of membrane combs known from DE 197 00 626 A1.

The invention has been explained in detail above with the aid of two embodiments. It is of course not restricted to the specific design of the embodiments. An important feature of the invention is that the sample pick-up surface 5 is bounded by a continuous edge, so that its area is clearly defined, by which means the sample pick-up volume is also determined, together with other parameters such as the depth and shape of the recess 7 and the nature of the sample liquid. The continuous edge may, as in the depicted embodiments, be formed by a body edge, with adjacent body areas of the sample dispenser abutting one another at a right-angle or at a smaller angle. The edge may however also be formed by a narrow annular web on a flat or curved surface. A further important aspect of the invention is the recess since, because of this feature and on account of the adhesion forces and the surface tension of the sample liquid, on the one hand reliable take-up of a predetermined quantity of sample liquid and on the other hand reliable transfer to a sample absorbing area are ensured.

LIST OF REFERENCE NUMBERS

1 sample dispenser body
2 shank section
3 transition section
4 tip
5 sample pick-up surface
6 edge
7 recess
8 longitudinal axis
9 hole
10 tapped hole
11 flattened surface

The invention claimed is:

1. A sample dispenser, for the application of liquid samples with a sample volume of less than 1 microliter on to a sample absorbing area, with a sample dispenser body having at its end a recess bounded by a continuous edge, such that, when the recess is dipped into a sample reservoir, a droplet of liquid sample of predetermined size adheres to the recess and by placing the recess on the sample absorbing area is completely dispensed, wherein the recess has a depth of less than 50% of its width, and wherein the recess has a shape selected from the group consisting of a hollow cone and a segmented hollow sphere.

2. Sample dispenser according to claim 1, wherein the hollow cone shaped recess is made by drilling.

3. Sample dispenser according to claim 2, wherein the recess is polished.

4. Sample dispenser according to claim 3, wherein the recess is a free end face of the sample dispenser body in the form of an elongated body.

5. Sample dispenser according to claim 4, wherein the sample dispenser body has as its tip a cylinder section having a diameter of from about 1.2 mm to about 1.7 mm.

6. Sample dispenser according to claim 4, wherein the sample dispenser body has as its tip a cylinder section with a diameter of from about 1 mm to about 2 mm.

7. Sample dispenser according to claim 6, wherein the cylinder section is provided with two parallel flattened walls, spaced from about 0.8 mm to about 1.2 mm apart.

8. Sample dispenser according to claim 1, wherein the recess is polished.

9. Sample dispenser according to claim 1, wherein the recess is a free end face of the sample dispenser body in the form of an elongated body.

10. Sample dispenser according to claim 1, wherein the sample dispenser body has at its tip a cylinder section having a diameter of from about 1.2 mm to about 1.7 mm.

11. The sample dispenser of claim 1, wherein the cylinder section comprises two flat parallel walls.

12. A sample dispenser, for the application of liquid samples with a sample volume of less than 1 microliter on to a sample absorbing area, with a sample dispenser body having at its end a recess bounded by a continuous edge, such that, when the recess is dipped into a sample reservoir, a droplet of liquid sample of predetermined size adheres to the recess and by placing the recess on the sample absorbing area is completely dispensed, wherein the recess has a depth of less than 50% of its width, wherein the recess has a shape selected from the group consisting of a hollow cone and a segmented hollow sphere, and wherein the sample dispenser body has as its tip a cylinder section with a diameter of from about 1 mm to about 2 mm.

13. Sample dispenser according to claim 12, wherein the cylinder section is provided with two parallel flattened walls, spaced from about 0.8 mm to about 1.2 mm apart.

14. The sample dispenser of claim 12, wherein the cylinder section comprises two flat parallel walls.

* * * * *